(12) United States Patent
Basha et al.

(10) Patent No.: US 10,254,368 B2
(45) Date of Patent: Apr. 9, 2019

(54) MAGNETIC RESONANCE IMAGING THAT NULLS SIGNALS FROM TWO OR MORE TISSUES TO BETTER DELINEATE AN INTERESTED TISSUE

(71) Applicant: BETH ISRAEL DEACONESS MEDICAL CENTER, Boston, MA (US)

(72) Inventors: Tamer Basha, Revere, MA (US); Reza Nezafat, Waban, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 53 days.

(21) Appl. No.: 15/548,691

(22) PCT Filed: Feb. 2, 2016

(86) PCT No.: PCT/US2016/016097
§ 371 (c)(1),
(2) Date: Aug. 3, 2017

(87) PCT Pub. No.: WO2016/126659
PCT Pub. Date: Aug. 11, 2016

(65) Prior Publication Data
US 2018/0031660 A1    Feb. 1, 2018

Related U.S. Application Data

(60) Provisional application No. 62/112,903, filed on Feb. 6, 2015.

(51) Int. Cl.
| | |
|---|---|
| A61B 5/055 | (2006.01) |
| G01R 33/56 | (2006.01) |
| G01R 33/483 | (2006.01) |

(52) U.S. Cl.
CPC .......... G01R 33/5602 (2013.01); A61B 5/055 (2013.01); G01R 33/483 (2013.01); *A61B 2576/023* (2013.01)

(58) Field of Classification Search
CPC .. G01R 33/5602; G01R 33/483; A61B 5/055; A61B 2576/023
(Continued)

(56) References Cited

U.S. PATENT DOCUMENTS

| | | |
|---|---|---|
| 5,655,531 A | 8/1997 | Nishimura et al. |
| 2009/0005673 A1 | 1/2009 | Rehwald et al. |

(Continued)

OTHER PUBLICATIONS

International Search Report and Written Opinion for International Patent Application No. PCT/US2016/016097 dated Jun. 27, 2016.
(Continued)

*Primary Examiner* — Farhana A Hoque
(74) *Attorney, Agent, or Firm* — Quarles & Brady LLP

(57) ABSTRACT

A system and method for acquiring magnetic resonance imaging (MRI) images with an MRI system is provided. The system and method directs the MRI system first to produce an inversion recovery radio frequency (RF) pulse, wait for a time period, produce a T2-preparation RF pulse, wait for another time period, and then acquire data of a part of a subject. The first produced RF pulse rotates net magnetization 180 degrees about an axis. The pulse sequence used to acquire data can be any two-dimensional or three-dimensional sequence used to acquire a volume in the subject. The two waiting time periods are chosen such that the signals of two or more tissues of the subject are nulled.

17 Claims, 4 Drawing Sheets

(58) Field of Classification Search
USPC .................................. 324/309, 322; 600/413
See application file for complete search history.

(56) References Cited

U.S. PATENT DOCUMENTS

2009/0270719 A1   10/2009   Miyoshi
2010/0191099 A1*   7/2010   Salerno .................. A61B 5/055
                                                            600/420

OTHER PUBLICATIONS

Xie et al., "3D Flow-Independent Peripheral Vessel Wall Imaging Using T2-Prepared Phase-Sensitive Inversion-Recovery Steady-State Free Precession." Journal of Magnetic Resonance Imaging 32:399-408 (2010), pp. 400-401 [online] <URL: http://onlinelibrary.wiley.com/doi/10.1002/jmri.22272/epdf>.

* cited by examiner

MAGNETIC RESONANCE IMAGING THAT NULLS SIGNALS FROM TWO OR MORE TISSUES TO BETTER DELINEATE AN INTERESTED TISSUE

CROSS-REFERENCE TO RELATED APPLICATIONS

This application represents the U.S. National Stage of International Application No. PCT/US2016/016097, filed Feb. 2, 2016 which claims the benefit of U.S. Provisional Patent Application Ser. No. 62/112,903, filed on Feb. 6, 2015, and entitled "System and Method for Magnetic Resonance Imaging That Nulls Signals from Two or More Tissues to Better Delineate an Interested Tissue."

STATEMENT REGARDING FEDERALLY SPONSORED RESEARCH

This invention was made with government support under EB008743 awarded by the National Institutes of Health. The government has certain rights in the invention.

BACKGROUND OF THE INVENTION

Magnetic resonance imaging ("MRI") is used to noninvasively assess the function of heart with good image quality and without risk of radiation. One major cardiac application is infarct imaging, imaging of infarcted tissue—scar—after a heart attack. Because scars can be small and with unknown shapes, it is desirable to control the MRI system so that the contrast between scar and all other major tissues in the heart in the generated images is maximized to a level that scar can be discernible from other major tissues.

It would therefore be highly desirable to provide a system and method for magnetic resonance imaging ("MRI") in which the contrast between scar and all other major tissues is maximized.

SUMMARY OF THE INVENTION

The present invention overcomes the aforementioned drawbacks by providing a method for using a magnetic resonance imaging (MRI) system to produce an image of a subject. The MRI system is operated to produce an inversion recovery (IR) radio frequency (RF) pulse and to wait a first delay time following the IR RF pulse. During this first delay time, magnetic resonance signals from a first tissue, a second tissue, and a third tissue in a subject positioned in the MRI system evolve according to respective longitudinal relaxation times for the first, second, and third tissues. The MRI system is then operated after the first delay time to produce a T2-preparation RF pulse having a duration and to wait a second delay time following the T2-preparation RF pulse. During this second delay time, magnetic resonance signals from the first, second, and third tissues in the subject evolve according to respective transverse relaxation times for the first, second, and third tissues. Data are then acquired from the subject with the MRI system during a data acquisition window following the second delay time. The first delay time, the duration of the T2-preparation RF pulse, and the second delay time are selected such that magnetic resonance signals from the first tissue and the second tissue are nulled during the data acquisition window. An image of the subject is then reconstructed from the acquired data. This reconstructed image depicts magnetic resonance signals from the third tissue and not from the first and second tissues.

It is another aspect of the invention to provide a method for generating an image of a subject with a magnetic resonance imaging (MRI) system. The method includes providing first, second, and third contrast maps to a computer system. The first, second, and third contrast maps have pixel values associated with magnetic resonance image contrast for a first, second, and third tissue, respectively, as a function of a first timing parameter that defines a duration of time between an IR RF pulse and a T2-preparation RF pulse and a second timing parameter that defines a duration of time between the T2-preparation RF pulse and a data acquisition window. The first, second, and third contrast maps are analyzed with the computer system to determine a combination of the first and second timing parameters that will result in maximum magnetic resonance signal from the third tissue while magnetic resonance signals from the first tissue and second tissue are simultaneously nulled. This combination of the first and second timing parameters is then communicated to an MRI system. The MRI system is operated to acquire data using a pulse sequence that includes an IR RF pulse, a T2-preparation pulse, and a data acquisition window spaced apart in time according to the combination of the first timing parameter and the second timing parameter. An image of the subject is reconstructed from the acquired data. This reconstructed image of the subject depicts the third tissue without signal contributions from the first and second tissues.

It is another aspect of the invention to provide a method for determining an optimal set of timing parameters for a magnetic resonance pulse sequence implementing an inversion recovery (IR) radio frequency (RF) pulse and a T2-preparation RF pulse. The method includes a first, second, and third contrast map to a computer system. The first, second, and third contrast maps have pixel values associated with magnetic resonance image contrast for a first, second, and third tissue, respectively, as a function of a first timing parameter that defines a duration of time between an IR RF pulse and a T2-preparation RF pulse, a second timing parameter that defines a duration of time between the T2-preparation RF pulse and a data acquisition window, and a third timing parameter that defines a duration of the T2-preparation RF pulse. The first, second, and third contrast maps are analyzed with the computer system to determine a set of the first, second, and third timing parameters that will result in maximum magnetic resonance signal from the third tissue while magnetic resonance signals from the first tissue and second tissue are simultaneously nulled. This set of the first, second, and third timing parameters is then stored as instructions to be provided to a magnetic resonance imaging (MRI) system.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
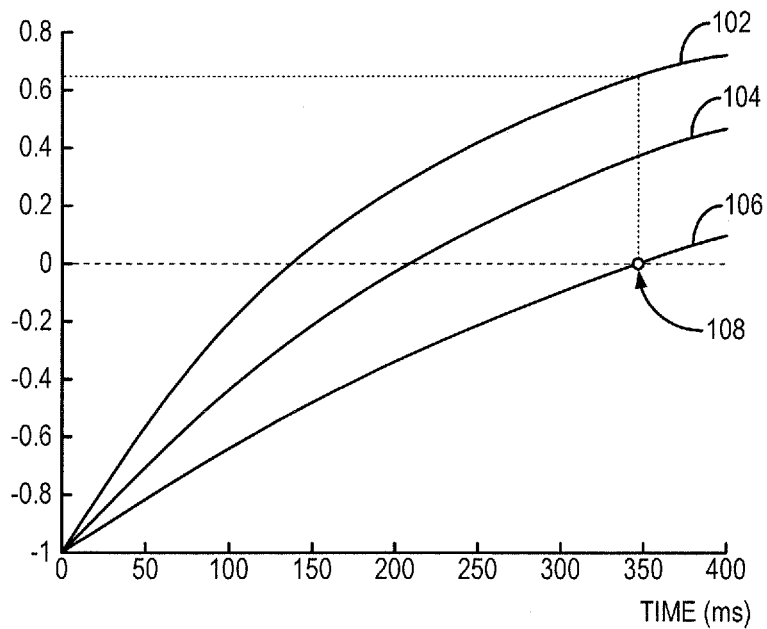
FIG. 1 is an example plot of signal intensities of tissues at various times after an inversion pulse when a standard late gadolinium enhancement (LGE) method is used.

Described here are systems and methods for magnetic resonance imaging ("MRI") using a pulse sequence that is designed such that signals originating from two or more particular tissue types are simultaneously nulled. The pulse sequence is preferably designed such that this simultaneous nulling is achieved while also maximizing image contrast for a desired tissue type. In this manner, the tissue-of-interest can be better delineated in the acquired magnetic resonance images.

As one non-limiting example, the pulse sequence can be designed to use an optimized combination of an inversion pulse and a $T_2$-preparation composite pulse to simultaneously null both healthy myocardium and blood signals, thereby producing a so-called black-blood ("BB") image without losing significant contrast between infarcted and healthy myocardial tissue. In general, this result is achieved using a pulse sequence that includes an inversion recovery pulse and a $T_2$-preparation pulse that are optimally timed and designed to simultaneously null the blood and healthy myocardium signals during a data acquisition window, while also maximizing the achievable signal from scar tissues.

For instance, a first delay time between the inversion pulse and the $T_2$-preparation pulse, the duration of the $T_2$-preparation pulse, and a second delay time between the $T_2$-preparation pulse and a data acquisition window are all selected such that signals from two particular tissue types (e.g., blood and healthy myocardial tissue in one example) are nulled during the data acquisition window. As will be described below, these timing parameters can be determined or estimated using numerical simulations, or by acquiring patient-specific data using a quick scouting sequence that samples the parameter space from which the optimal timing parameters can be determined. An example of an MRI system that can implement these methods is described below with respect to FIG. 6.

As described above, MRI can be used to image and detect scar tissue in an infarcted heart. Three major types of tissues are present in a infarcted heart: blood, healthy myocardium, and scar tissue. To discern scar tissue from its surroundings, contrast between scar and all other tissues should be increased to a desirable level. For example, it is desirable if scar tissue can be made to appear significantly brighter in an image than blood and healthy myocardium. Such contrast would allow scar tissue to be assessed with confidence.

Late gadolinium enhancement ("LGE") imaging is a standard MRI method for infarct imaging. LGE can be used to depict scar and fibrosis in patients with cardiovascular diseases. In LGE, a gadolinium-containing contrast agent is administered to a subject, such as via an intravenous injection. The contrast agent diffuses rapidly out of capillaries into tissue, but cannot cross intact cell membranes. After the intravenous bolus, both healthy myocardium and scar tissue passively accumulate contrast agent. But, with time the scar tissue will possess a slightly larger amount of contrast agent per unit volume of tissue because of the contrast agent slower kinetics and larger volume for distribution.

The MRI pulse sequence typically used in LGE often starts with an inversion recovery ("IR") radio frequency ("RF") pulse. Gadolinium-containing contrast agents are $T_1$-shortening agents, which means that tissues in the presence of the agents will experience shorter $T_1$ than the tissues not near the agents. Referring to FIG. 1, the normalized net magnetization of three different tissues (scar, blood, and healthy myocardium) at various times after the end of the IR pulse is plotted. The magnetization recovery curves for these tissues are illustrated as line 102 for scar tissue, line 104 for blood, and line 106 for healthy myocardium. Immediately after the IR pulse is applied, the net magnetization is $-M_0$. Afterwards, the magnetization recovers back to $M_0$ according to an exponential function with a time constant $T_1$. As described above, because of having a larger volume of contrast agents per unit, scar (line 102) has shorter $T_1$ than myocardium (line 106). The acquisition time of LGE is often chosen at the nulling point of myocardium so that myocardium appears black and scar appears bright. This way, a contrast difference between myocardium and scar based on $T_1$ is created.

But, blood (line 104) also appears bright in the images acquired with standard LGE. In fact, blood and scar have similar $T_1$ values, so the contrast between blood and scar is not sufficient to differentiate the two tissues. Referring still to FIG. 1, the blood signal is around 75 percent of the scar signal at the myocardium null point 108 (i.e., the contrast between blood and scar tissue is low). This low contrast makes sub-endocardial scar challenging to depict and detect, especially in thin structures such as right ventricle or left atrium. Other methods have been used in attempt to increase the blood-scar contrast, but suffer from either reduced SNR or reduced scar-myocardium contrast. Moreover, most of these techniques are not compatible with three-dimensional ("3D") acquisitions, which have recently emerged to completely cover the heart in viability imaging.

The systems and methods described here combine an inversion pulse and a $T_2$-preparation composite pulse that are optimally timed and designed to simultaneously null two tissue types, while maximizing contrast with a third tissue type. As one non-limiting example, the pulse sequence can be designed to simultaneously null signals from blood and healthy myocardium, while maximizing the signal intensity achievable in scar tissue, and thus significantly increasing the image contrast between scar tissue and blood and healthy myocardium. In general, the $T_2$-preparation pulse is inserted between the inversion pulse and the data acquisition and the temporal spacing between the two RF pulses and the data acquisition, in addition to the duration of the $T_2$-preparation pulse, are designed to achieve the results described above.

Figure 2:
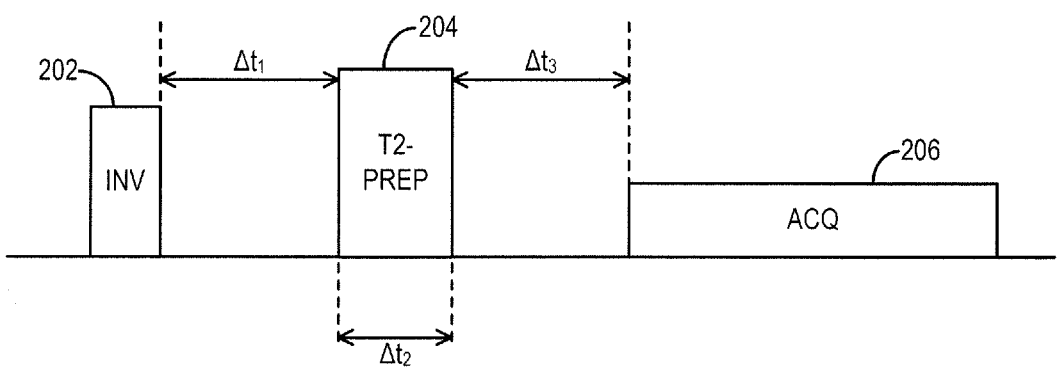
FIG. 2 is an example of a pulse sequence that may be used to implement the system and method as disclosed herein.

FIG. 2 illustrates an example of a pulse sequence that implements the techniques described above. The pulse sequence includes applying an inversion pulse 202 before applying a $T_2$-preparation pulse 204 and implementing a data acquisition 206. The inversion pulse 202 may be accompanied with a slice-selective or slab-selective gradient, or may be a non-slice-selective or non-slab-selective RF pulse. After a time period, $\Delta t_1$, the $T_2$-preparation 204 is applied. The $T_2$-preparation lasts for a duration of time, $\Delta t_2$. The $T_2$-preparation pulse 204 may be a composite $T_2$-preparation pulse sequence that includes a series of RF pulses starting with a 90 degree RF pulse, followed by a train of 180 degree RF pulses, and ending with a −90 degree RF pulse. In this example, the train of 180 degree RF pulses are used to remove $T^*_2$ effects.

Figure 3:
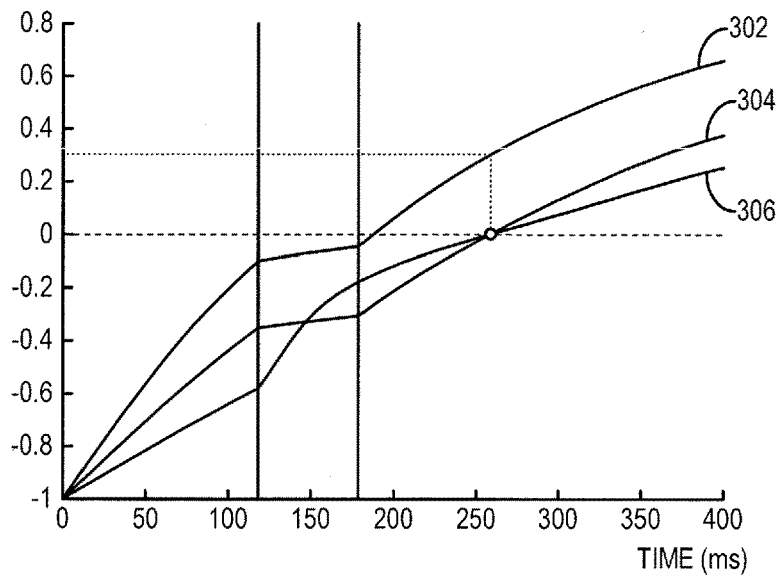
FIG. 3 is an example plot of signal intensities of tissues at various times after an inversion pulse when a system and method as disclosed herein is used.

When applying a $T_2$-preparation pulse, the signals from the tissues also evolve according to an exponential function described by a different time constant, the transverse relaxation time, $T_2$. FIG. 3 illustrates the magnetization recovery curves for three different tissues (scar tissue, 302; blood, 304; and healthy myocardium, 306) during the application of an inversion pulse and $T_2$-preparation pulse according to the methods described above. Blood (line 304) has shorter $T_1$ than healthy myocardium (line 306), so during the time period, $\Delta t_1$, after the inversion pulse but before the $T_2$-preparation pulse, blood (line 304) recovers faster than healthy myocardium (line 306). But, blood (line 304) has a longer $T_2$ than healthy myocardium (line 306), so when a $T_2$" preparation pulse is applied during the time period, $\Delta t_2$, the blood signal (line 304) evolves slower than the healthy myocardium signal (line 306), thereby reversing the faster recovery that occurred during the first time period, $\Delta t_1$. After the $T_2$-preparation pulses are turned off, the magnetization once again begins recovering to the longitudinal axis and continues the inversion recovery according to the longitudinal relaxation time, $T_1$, of the tissues. With the adjustment of the time periods $\Delta t_1$, $\Delta t_2$, and $\Delta t_3$, both blood (line 304) and healthy myocardium (line 306) signals can be nulled at a nulling time point 308 at which the signals from scar tissue (line 302) are not nulled. Data acquisition can thus occur at this nulling time point 308. Preferably, the timing parameters ($\Delta t_1$, $\Delta t_2$, $\Delta t_3$) are selected to both simultaneously null the signals from blood and healthy myocardium, while maximizing the achievable signal from scar tissue. In this manner, the acquired images will depict blood and healthy myocardium as black, and scar tissue as bright. As a result, scar tissue can be more readily differentiated from the other tissues in the heart. By changing the time periods $\Delta t_1$, $\Delta t_2$, $\Delta t_3$, one can control the contrast between different tissues in the heart.

Referring again to FIG. 2, after the $T_2$-preparation pulses end, the MRI system waits for a time period $\Delta t_3$ so that signals from two or more tissues are simultaneously nulled at a nulling time point. Data is acquired during a data acquisition window 206 that is timed to occur while signals from these two or more tissues (e.g., blood and healthy myocardium) are simultaneously nulled, as mentioned above. Data acquisition can be performed using any suitable data acquisition sequence, including any two-dimensional or three-dimensional pulse sequences used to acquire images of a volume in a subject.

Figure 4:
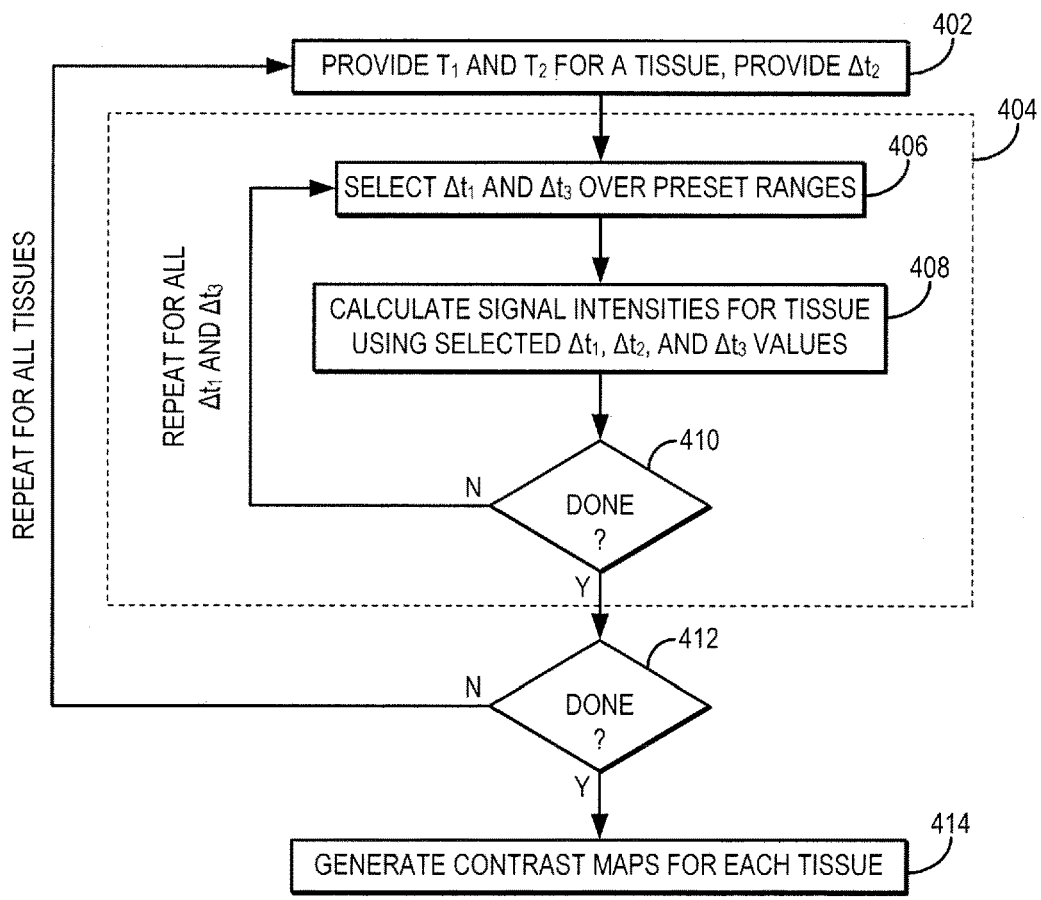
FIG. 4 is a example flowchart that may be used to simulate the effects of $\Delta t_1$, $\Delta t_2$, and $\Delta t_3$ on signal intensities of tissues.

As described above, numerical simulations can be performed using the Bloch equation to determine or estimate values for $\Delta t_1$, $\Delta t_2$, and $\Delta t_3$. Referring now to FIG. 4, an flowchart is illustrated as setting forth the steps of an example method for estimating these timing parameters. The method begins by providing $T_1$ and $T_2$ values for a specific tissue-of-interest, in addition to an initial value for the timing parameter, $\Delta t_2$, which is the duration of the $T_2$-preparation pulse, as indicated at step 402. For this tissue-of-interest, the steps shown generally at 404 are performed next. First, a set of values for $\Delta t_1$ and $\Delta t_3$ are provided, as indicated at step 406, and then signal intensities for the tissue-of-interest are calculated using a combination of values for $\Delta t_1$ and $\Delta t_3$ from this provided set and using the provided $\Delta t_2$ value, as indicated at step 408. This process 404 is then repeated for all combinations of $\Delta t_1$ and $\Delta t_3$ within the set of values, which may span preset ranges for each timing parameter.

When a determination is made at decision block 410 that signal intensities have been estimated for all desired combinations of $\Delta t_1$ and $\Delta t_3$ within the set of values, a determination is made at decision block 412 whether signal intensities have been estimated for all of the desired tissues-of-interest. If not, the method loops back to step 402, where $T_1$ and $T_2$ values for a different tissue-of-interest, in addition to an initial value for the timing parameter, $\Delta t_2$, are provided. The process at 404 is then repeated for each desired tissue-of-interest until the signal intensities for all desired tissues-of-interest have been estimated, or otherwise simulated, for all desired combinations of $\Delta t_1$ and $\Delta t_3$ within the set of values. When the signal intensities for all desired tissues-of-interest have been estimated, or otherwise simulated, for all desired combinations of $\Delta t_1$ and $\Delta t_3$ within the set of values, contrast maps are generated to depict the contrast for a particular tissue type given a combination of time period parameters, $\Delta t_1$ and $\Delta t_3$, for each tissue-of-interest.

In some embodiments, step 402 and process 404 are also repeated for multiple different $T_2$-preparation pulse durations, $\Delta t_2$, within a desired range of such values. In these embodiments, the contrast maps generated in step 414 are three-dimensional maps of contrast at various combinations of $\Delta t_1$, $\Delta t_2$ and $\Delta t_3$. In these instances, the contrast maps provide information about the behavior of signal intensities, and the resulting image contrast, for various tissues-of-interest as a function of a three-dimensional parameter space defined by the timing parameters, $\Delta t_1$, $\Delta t_2$ and $\Delta t_3$.

As will be described below, the contrast maps generated in the manner mentioned above provide information about the magnetization recovery (and thus signal intensity evolution) over a two-dimensional or three-dimensional parameter space defined by combinations of the timing parameters $\Delta t_1$, $\Delta t_2$ and $\Delta t_3$. Thus, these contrast maps can be efficiently analyzed to identify combinations of timing parameters that, when implemented in a pulse sequence such as the one illustrated in FIG. 2, can allow for the acquisition of magnetic resonance images in which signals are nulled from two particular tissue types while optimizing the contrast available for a third tissue type that is of clinical interest. In the examples described above, this analysis can be performed to identify a combination of timing parameters that result in signals being nulled from blood and healthy myocardium while optimizing the available signal intensity from scar tissue.

Figures 5A, 5B:
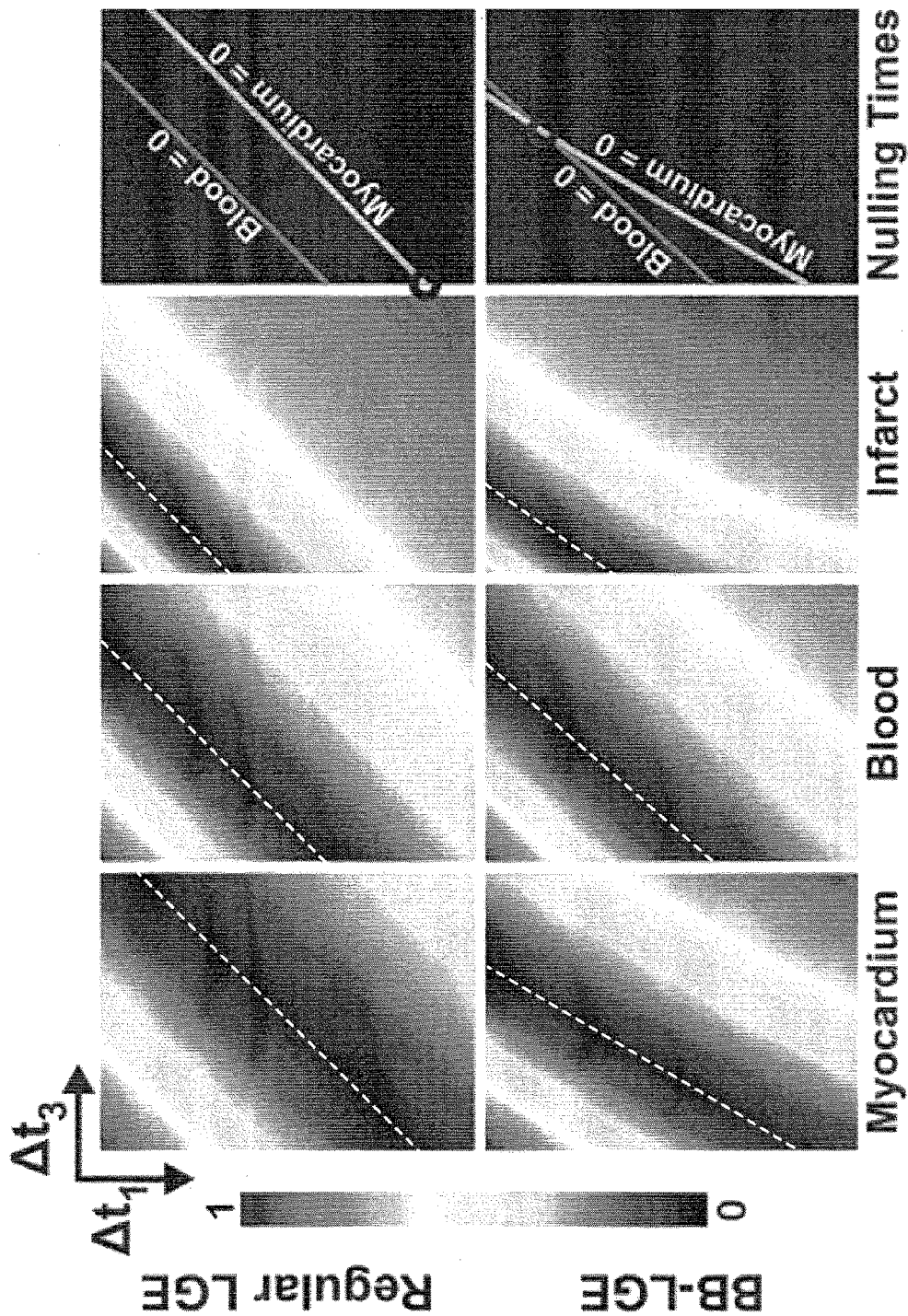
FIG. 5A depicts example contrast maps at various $\Delta t_1$ and $\Delta t_3$ values for different tissue types using a preset $T_2$-preparation pulse duration.
FIG. 5B depicts tissue nulling lines derived from the contrast maps of FIG. 5A and that indicate a combination of $\Delta t_1$ and $\Delta t_3$ values that will simultaneously null two particular tissue types at a nulling time point.

Referring now to FIG. 5A, examples of contrast maps generated using the methods described above are illustrated. The top panels depict maps generated using a standard LGE pulse sequence (i.e., $\Delta t_2=0$), and the bottom panels depict contrast maps generated when using the methods described here. In this particular example, the contrast maps are two-dimensional parameter space maps for a preset $T_2$-preparation pulse duration, $\Delta t_2$, of 35 ms. In FIG. 5A, the white dashed line in each contrast map indicates the so-called null signal line, along which the combination of $\Delta t_1$ and $\Delta t_3$ results in signals from that particular tissue type being nulled during data acquisition.

In FIG. 5B, the null signal lines of healthy myocardium and blood are illustrated. As shown in the top panel of FIG. 5B, when a standard LGE sequence is used, the null signal lines of healthy myocardium and blood do not intersect at a common point, thereby preventing simultaneous nulling of both tissues. But, when the method described here is used, a common null point can be obtained (shown in the bottom panel of FIG. 5B). Identifying this intersection point results in determining the $\Delta t_1$ and $\Delta t_3$ parameters that will result in simultaneously nulling the signals from blood and healthy myocardium during the data acquisition window.

As the value for $\Delta t_2$ is changed, so does the location of the signal nulling lines. Thus, some combinations of $\Delta t_1$, $\Delta t_2$, and $\Delta t_3$ may not result in an intersection between the signal nulling lines for any two particular tissues (e.g., blood and healthy myocardium). Similarly, some combinations of $\Delta t_1$, $\Delta t_2$, and $\Delta t_3$ will result in higher signal intensities from a third tissue-of-interest (e.g., scar tissue) than others. A search through the $\Delta t_1$, $\Delta t_2$, and $\Delta t_3$ parameter space can thus determine the optimal set of parameters that results in simultaneously nulling two particular tissue types (e.g., blood and healthy myocardial) while also maximizing the achievable signal from a third tissue-of-interest (e.g., scar tissue). It will be readily appreciated that the methods described here can be readily adapted to any combination of tissue types. That is, contrast maps can be generated for any desirable combination of tissue types and the timing parameter space for these tissues can be searched to identify the combination of timing parameters that results in the desired image contrast for a particular clinical or research application.

Compared to standard LGE methods, there is a decrease in the scar signal intensities in the images acquired at the healthy myocardium-blood common null point with the method described here. The amount of decrease depends on $\Delta t_2$. Referring back to FIG. 3, the recovery of scar signals slows down during $\Delta t_2$. So, shorter $\Delta t_2$ may yield less decrease in scar signals. But, $\Delta t_2$ should be long enough to allow recovery of myocardium that surpasses that of blood, such that both signals can be nulled after the $T_1$ recovery during $\Delta t_3$.

In some embodiments, rather than performing or relying upon previously performed numerical simulations, a quick scouting sequence may be used to determine the timing parameters for the nulling point before the entire volume is imaged. For example, during scouring, the pulse sequence for the system and method as disclosed herein (shown in FIG. 2) can be repeated for various $\Delta t_1$, $\Delta t_2$, or $\Delta t_3$ values. This scouting sequence can be performed over the entire imaging volume, or a subset thereof, including only a single slice. The scanning parameters for scouting images with desired tissues nulled and with desired signal to noise ratios are chosen as scanning parameters used to image the entire volume with the system and method as disclosed herein.

In one configuration, the computer program used for simulations as described above may also be used to determine optimal $\Delta t_1$, $\Delta t_2$ or $\Delta t_3$ for the nulling time point of two or more tissues. A quick scan can be used to measure the $T_1$ and $T_2$ for each tissue, or predetermined values for the desired tissue types can be used. Then these $T_1$ and $T_2$ values are inputted to the method in step 402 in FIG. 4. Using the contrast maps generated in step 414 or the signals computed in step 408, optimal $\Delta t_1$, $\Delta t_2$, or $\Delta t_3$ values can be generated with signals of two or more tissues nulled while the signals of the remaining tissues still haven desirable signal to noise ratios.

Heart and its major tissues—myocardium, blood, and scar—are used herein as examples to illustrate the present system and method. One skilled in the art would appreciate that the system and method disclosed herein may be applied to image other parts of a subject with desired contrast among tissues. Also, with certain combinations of $\Delta t_1$, $\Delta t_2$, and $\Delta t_3$, signals from more than two tissues may be nulled. In addition, for the purpose of comparison with standard LGE method, gadolinium-containing contrast agents are described herein. One skilled in art would appreciate that the system and method disclosed herein does not require contrast agents to be used during imaging.

Figure 6:
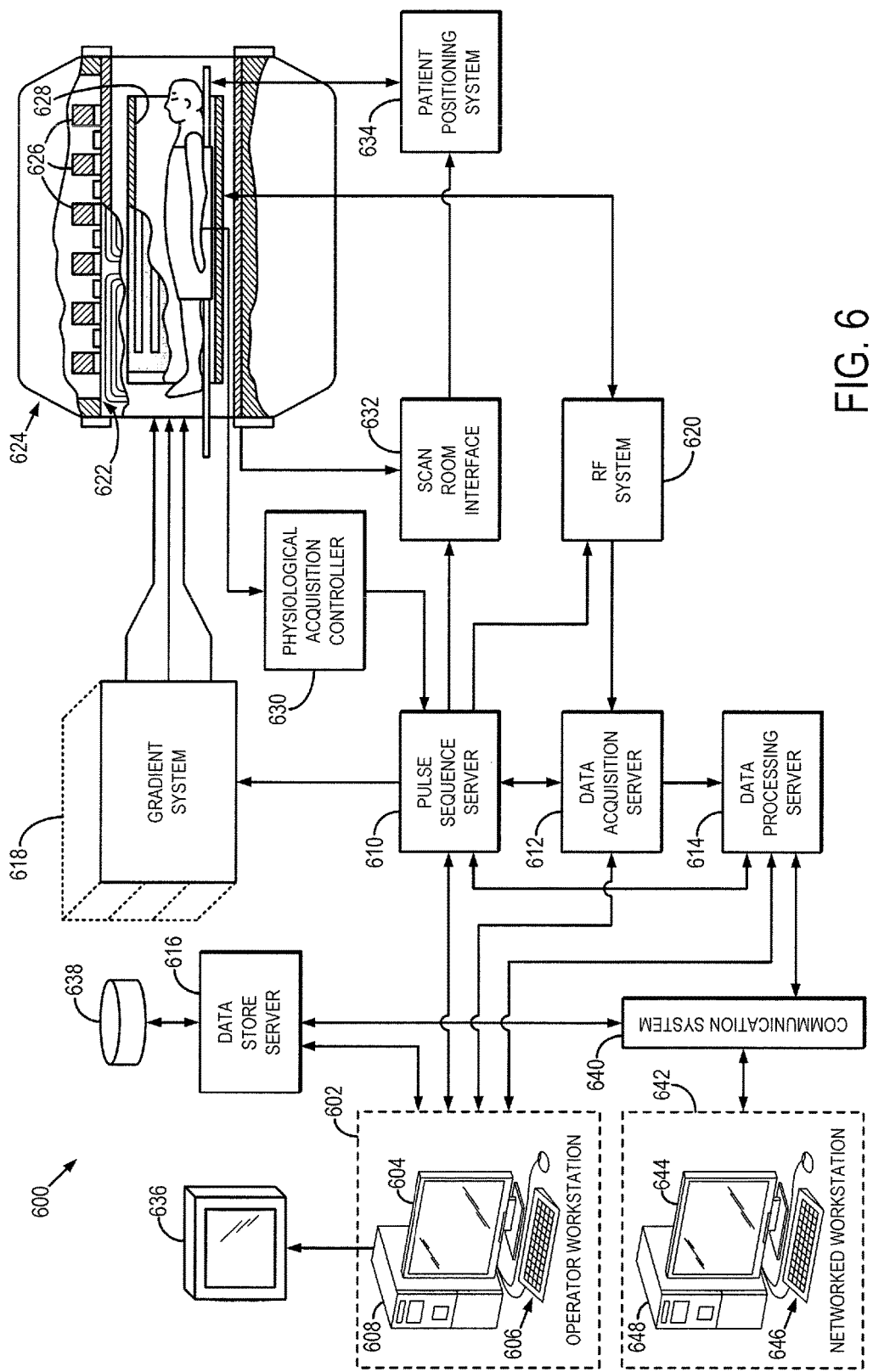
FIG. 6 is a block diagram of an example of a magnetic resonance imaging ("MRI") system.

Referring particularly now to FIG. 6, an example of a magnetic resonance imaging ("MRI") system 600 is illustrated. The MRI system 600 includes an operator workstation 602, which will typically include a display 604; one or more input devices 606, such as a keyboard and mouse; and a processor 608. The processor 608 may include a commercially available programmable machine running a commercially available operating system. The operator workstation 602 provides the operator interface that enables scan prescriptions to be entered into the MRI system 600. In general, the operator workstation 602 may be coupled to four servers: a pulse sequence server 610; a data acquisition server 612; a data processing server 614; and a data store server 616. The operator workstation 602 and each server 610, 612, 614, and 616 are connected to communicate with each other. For example, the servers 610, 612, 614, and 616 may be connected via a communication system 640, which may include any suitable network connection, whether wired, wireless, or a combination of both. As an example, the communication system 640 may include both proprietary or dedicated networks, as well as open networks, such as the internet.

The pulse sequence server 610 functions in response to instructions downloaded from the operator workstation 602 to operate a gradient system 618 and a radiofrequency ("RF") system 620. Gradient waveforms necessary to perform the prescribed scan are produced and applied to the gradient system 618, which excites gradient coils in an assembly 622 to produce the magnetic field gradients $G_x$, $G_y$, and $G_z$ used for position encoding magnetic resonance signals. The gradient coil assembly 622 forms part of a magnet assembly 624 that includes a polarizing magnet 626 and a whole-body RF coil 628.

RF waveforms are applied by the RF system 620 to the RF coil 628, or a separate local coil (not shown in FIG. 6), in order to perform the prescribed magnetic resonance pulse sequence. Responsive magnetic resonance signals detected by the RF coil 628, or a separate local coil (not shown in FIG. 6), are received by the RF system 620, where they are amplified, demodulated, filtered, and digitized under direction of commands produced by the pulse sequence server 610. The RF system 620 includes an RF transmitter for producing a wide variety of RF pulses used in MRI pulse sequences. The RF transmitter is responsive to the scan prescription and direction from the pulse sequence server 610 to produce RF pulses of the desired frequency, phase, and pulse amplitude waveform. The generated RF pulses may be applied to the whole-body RF coil 628 or to one or more local coils or coil arrays (not shown in FIG. 6).

The RF system 620 also includes one or more RF receiver channels. Each RF receiver channel includes an RF preamplifier that amplifies the magnetic resonance signal received by the coil 628 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \tag{1};$$

and the phase of the received magnetic resonance signal may also be determined according to the following relationship:

$$\varphi = \tan^{-1}\left(\frac{Q}{I}\right). \quad (2)$$

The pulse sequence server 610 also optionally receives patient data from a physiological acquisition controller 630. By way of example, the physiological acquisition controller 630 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 610 to synchronize, or "gate," the performance of the scan with the subject's heart beat or respiration.

The pulse sequence server 610 also connects to a scan room interface circuit 632 that receives signals from various sensors associated with the condition of the patient and the magnet system. It is also through the scan room interface circuit 632 that a patient positioning system 634 receives commands, to move the patient to desired positions during the scan.

The digitized magnetic resonance signal samples produced by the RF system 620 are received by the data acquisition server 612. The data acquisition server 612 operates in response to instructions downloaded from the operator workstation 602 to receive the real-time magnetic resonance data and provide buffer storage, such that no data is lost by data overrun. In some scans, the data acquisition server 612 does little more than pass the acquired magnetic resonance data to the data processor server 614. However, in scans that require information derived from acquired magnetic resonance data to control the further performance of the scan, the data acquisition server 612 is programmed to produce such information and convey it to the pulse sequence server 610. For example, during prescans, magnetic resonance data is acquired and used to calibrate the pulse sequence performed by the pulse sequence server 610. As another example, navigator signals may be acquired and used to adjust the operating parameters of the RF system 620 or the gradient system 618, or to control the view order in which k-space is sampled. In still another example, the data acquisition server 612 may also be employed to process magnetic resonance signals used to detect the arrival of a contrast agent in a magnetic resonance angiography ("MRA") scan. By way of example, the data acquisition server 612 acquires magnetic resonance data and processes it in real-time to produce information that is used to control the scan.

The data processing server 614 receives magnetic resonance data from the data acquisition server 612 and processes it in accordance with instructions downloaded from the operator workstation 602. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 614 are conveyed back to the operator workstation 602 where they are stored. Real-time images are stored in a data base memory cache (not shown in FIG. 6), from which they may be output to operator display 602 or a display 636 that is located near the magnet assembly 624 for use by attending physicians. Batch mode images or selected real time images are stored in a host database on disc storage 638. When such images have been reconstructed and transferred to storage, the data processing server 614 notifies the data store server 616 on the operator workstation 602. The operator workstation 602 may be used by an operator to archive the images, produce films, or send the images via a network to other facilities.

The MRI system 600 may also include one or more networked workstations 642. By way of example, a networked workstation 642 may include a display 644; one or more input devices 646, such as a keyboard and mouse; and a processor 648. The networked workstation 642 may be located within the same facility as the operator workstation 602, or in a different facility, such as a different healthcare institution or clinic.

The networked workstation 642, whether within the same facility or in a different facility as the operator workstation 602, may gain remote access to the data processing server 614 or data store server 616 via the communication system 640. Accordingly, multiple networked workstations 642 may have access to the data processing server 614 and the data store server 616. In this manner, magnetic resonance data, reconstructed images, or other data may be exchanged between the data processing server 614 or the data store server 616 and the networked workstations 642, such that the data or images may be remotely processed by a networked workstation 642. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for using a magnetic resonance imaging (MRI) system to produce an image of a subject, the steps of the method comprising:
   (a) producing with the MRI system, an inversion recovery (IR) radio frequency (RF) pulse;
   (b) waiting a first delay time following the IR RF pulse during which magnetic resonance signals from a first tissue, a second tissue, and a third tissue in a subject positioned in the MRI system evolve according to respective longitudinal relaxation times for the first, second, and third tissues;
   (c) producing with the MRI system after the first delay time, a T2-preparation RF pulse having a duration;
   (d) waiting a second delay time following the T2-preparation RF pulse during which magnetic resonance signals from the first, second, and third tissues in the subject evolve according to respective transverse relaxation times for the first, second, and third tissues;
   (e) acquiring data from the subject with the MRI system during a data acquisition window following the second delay time, wherein the first delay time, the duration of the T2-preparation RF pulse, and the second delay time are selected such that magnetic resonance signals from the first tissue and the second tissue are nulled during the data acquisition window;
   (f) reconstructing an image of the subject from the acquired data, wherein the reconstructed image depicts magnetic resonance signals from the third tissue and not from the first and second tissues.

2. The method as recited in claim 1, further comprising:
generating a contrast map for each of the first, second, and third tissues, each contrast map depicting magnetic resonance image contrast values for respective ones of the first, second, and third tissues as a function of different values for the first delay time, the duration of the T2-preparation RF pulse, and the second delay time; and wherein steps (a)-(c) include selecting the first delay time, the duration of the T2-preparation RF pulse, and the second delay time based on the generated contrast maps for the first, second, and third tissues.

3. The method as recited in claim 2, wherein generating the contrast maps for the first, second, and third tissues includes acquiring data from the subject with the MRI system over a range of different values for the first delay time, the duration of the T2-preparation RF pulse, and the second delay time.

4. The method as recited in claim 2, wherein generating the contrast maps for the first, second, and third tissues includes generating the contrast maps using a numerical simulation based on magnetic resonance signal models for each of the first, second, and third tissues.

5. The method as recited in claim 2, wherein the first delay time, the duration of the T2-preparation RF pulse, and the second delay time are further selected to maximize magnetic resonance signals from the third tissue during the data acquisition window while magnetic resonance signals from the first tissue and the second tissue are nulled during the data acquisition window.

6. The method as recited in claim 1, wherein the first tissue is blood, the second tissue is myocardium, and the third tissue is infarcted myocardium.

7. The method as recited in claim 1, wherein the T2-preparation RF pulse is a composite RF pulse.

8. The method as recited in claim 7, wherein the composite RF pulse includes a 90 degree RF pulse followed by a train of 180 degree RF pulses followed by a −90 degree RF pulse.

9. A method for generating an image of a subject with a magnetic resonance imaging (MRI) system, the steps of the method comprising:
(a) providing to a computer system:
a first contrast map having pixel values associated with magnetic resonance image contrast for a first tissue as a function of a first timing parameter that defines a duration of time between an inversion recovery (IR) radio frequency (RF) pulse and a T2-preparation RF pulse and a second timing parameter that defines a duration of time between the T2-preparation RF pulse and a data acquisition window;
a second contrast map having pixel values associated with magnetic resonance image contrast for a second tissue as a function of the first timing parameter and the second timing parameter; and
a third contrast map having pixel values associated with magnetic resonance image contrast for a third tissue as a function of the first timing parameter and the second timing parameter;
(b) analyzing the first, second, and third contrast maps with the computer system to determine a combination of the first timing parameter and second timing parameter that will result in maximum magnetic resonance signal from the third tissue while magnetic resonance signals from the first tissue and second tissue are simultaneously nulled;

(c) communicating the combination of the first timing parameter and the second timing parameter to an MRI system;
(d) acquiring data with the MRI system using a pulse sequence that includes an IR RF pulse, a T2-preparation pulse, and a data acquisition window spaced apart in time according to the combination of the first timing parameter and the second timing parameter; and
(e) reconstructing an image of the subject from the acquired data, wherein the image of the subject depicts the third tissue without signal contributions from the first and second tissues.

10. The method as recited in claim 9, wherein the first, second, and third contrast maps are provided by performing numerical simulations that estimate magnetic resonance image contrast at a plurality of different first and second timing parameters.

11. The method as recited in claim 9, wherein:
the first, second, and third contrast maps are three-dimensional maps that have pixel values associated with magnetic resonance image contrast for the first, second, and third tissues, respectively, as a function of the first timing parameter, the second timing parameter, and a third timing parameter that defines a duration of the T2-preparation RF pulse; and
step (b) includes analyzing the first, second, and third contrast maps with the computer system to determine a combination of the first, second, and third timing parameters.

12. The method as recited in claim 9, wherein step (b) includes identifying the combination of the first and second timing parameters by identifying a common pixel location in the contrast map for the first tissue and the contrast map for the second tissue at which magnetic resonance signals from the first and second tissues are both nulled.

13. The method as recited in claim 12, wherein step (b) includes identifying a plurality of combinations of the first and second timing parameters at which magnetic resonance signals from the first and second tissues are both nulled and then identifying the combination of the first and second timing parameters from this plurality of combinations that maximizes magnetic resonance signals from the third tissue.

14. The method as recited in claim 9, wherein the first tissue is blood, the second tissue is myocardium, and the third tissue is infarcted myocardium.

15. A method for determining an optimal set of timing parameters for a magnetic resonance pulse sequence implementing an inversion recovery radio frequency (RF) pulse and a T2-preparation RF pulse, the steps of the method comprising:
(a) providing to a computer system:
a first contrast map having pixel values associated with magnetic resonance image contrast for a first tissue as a function of a first timing parameter that defines a duration of time between an inversion recovery (IR) radio frequency (RF) pulse and a T2-preparation RF pulse, a second timing parameter that defines a duration of time between the T2-preparation RF pulse and a data acquisition window, and a third timing parameter that defines a duration of the T2-preparation RF pulse;
a second contrast map having pixel values associated with magnetic resonance image contrast for a second tissue as a function of the first, second, and third timing parameters; and a third contrast map having pixel values associated with magnetic resonance image contrast for a third tissue as a function of the first, second, and third timing parameters;

(b) analyzing the first, second, and third contrast maps with the computer system to determine a set of the first, second, and third timing parameters that will result in maximum magnetic resonance signal from the third tissue while magnetic resonance signals from the first tissue and second tissue are simultaneously nulled; and (c) storing the set of the first, second, and third timing parameters as instructions to be provided to a magnetic resonance imaging (MRI) system.

16. The method as recited in claim 15, wherein step (b) includes searching a parameter space defined by the first, second, and third timing parameters for each of the first, second, and third tissues to determine the combination of the first, second, and third timing parameters.

17. The method as recited in claim 15, wherein the first tissue is blood, the second tissue is myocardium, and the third tissue is infarcted myocardium.

\* \* \* \* \*